United States Patent [19]

Lubecki et al.

[11] 4,388,530
[45] Jun. 14, 1983

[54] PROCESS AND APPARATUS FOR THE CONTINUOUS MEASUREMENT OF ELEMENT CONTENTS

[75] Inventors: Andrzej Lubecki, Stutensee-Bl.; Kurt Wiese, Stutensee-Büchig; Karl Winkler, Steinweiler, all of Fed. Rep. of Germany

[73] Assignee: Kernforschungszentrum Karlsruhe Gesellschaft mit beschrankter Haftung, Karlsruhe, Fed. Rep. of Germany

[21] Appl. No.: 141,698

[22] Filed: Apr. 18, 1980

[30] Foreign Application Priority Data

Apr. 20, 1979 [DE] Fed. Rep. of Germany ....... 2915986

[51] Int. Cl.³ .......................... G01N 23/20; G21K 1/00
[52] U.S. Cl. ................................. 378/45; 250/358 R; 250/434; 378/83
[58] Field of Search ........... 250/272, 273, 274, 277 R, 250/434, 435, 510, 358, 359, 360

[56] References Cited

U.S. PATENT DOCUMENTS

| | | | |
|---|---|---|---|
| 2,999,937 | 9/1961 | Kohler | 250/358 R |
| 3,270,200 | 8/1966 | Rhodes | 250/358 R |
| 3,443,092 | 5/1969 | Carr-Brin et al. | 250/277 |
| 3,746,874 | 7/1973 | Ohata et al. | |
| 4,125,769 | 11/1978 | Marten et al. | 250/272 |
| 4,180,735 | 12/1979 | Sipilä et al. | 250/434 |

FOREIGN PATENT DOCUMENTS

| | | |
|---|---|---|
| 1227697 | 10/1966 | Fed. Rep. of Germany . |
| 2049500 | 11/1977 | Fed. Rep. of Germany . |
| 998196 | 7/1965 | United Kingdom . |
| 1127342 | 9/1968 | United Kingdom . |
| 1158871 | 7/1969 | United Kingdom . |

*Primary Examiner*—Bruce C. Anderson
*Attorney, Agent, or Firm*—Spencer & Kaye

[57] ABSTRACT

A method and apparatus for continuous measurement, by X-ray fluorescence analysis, of the elemental content of a slurry, independently of slurry density and slurry composition. The slurry, a source of primary radiation, a target, and a detector are arranged so that the slurry passes between the source and the detector, and a portion of the primary radiation excites the elements in the slurry to emit elemental X-ray radiation. The primary radiation also excites the target, to emit target radiation which passes through the slurry. The primary, target, and elemental radiations are absorbed by the detector, and the absorbed radiations are evaluated to determine the elemental content of the slurry.

22 Claims, 7 Drawing Figures

PROCESS AND APPARATUS FOR THE CONTINUOUS MEASUREMENT OF ELEMENT CONTENTS

BACKGROUND OF THE INVENTION

The present invention relates to a process and an apparatus for the continuous measurement of element contents in slurries independently of slurry density and slurry composition, by use of the X-ray fluorescence analysis method (XRFA).

Due to the rising worldwide need for raw materials, it is increasingly necessary nowadays to mine deposits with a low content of the desired raw material. Such deposits are primarily exploited with the use of the flotation method, wherein the desired, valuable mineral is obtained from an aerated suspension of finely ground raw minerals and water, a so-called flotation slurry, with the aid of chemicals. To be able to operate facilities using this method, frequently with widely branched-out slurry conduits, in an economical manner, a continuous analysis of the product streams is of decisive importance. Therefore, analytical devices are required which, with maximum speed, indicate the mineral contents of interest at strategically important points in the process and thereby make it possible to quickly intervene in the operation of the process. This is necessary, in particular, when monitoring the waste streams and the concentrate streams leaving the production facility. Losses of valuable minerals in the waste stream mean considerable financial setbacks in the operation of such a facility.

Further, the quality requirements posed by the processing industry using the resultant concentrates are currently very high and can be met only with difficulty. Only a rapid, continuous quality control affords the possibility to extensively preclude impaired production by a controlled intervention in the process operation. The posed requirements not only relate to providing concentrates with a specific content of valuable mineral, but also to providing the concentrates with precise proportional values for so-called deleterious components. Exceeding such proportional values can lead to considerable financial losses and/or to a discarding of the entire product.

It is even currently still quite customary, especially in relatively small flotation plants, to conduct the control of the process streams by means of wet chemical analysis. These analysis methods cannot be effected continuously and require a considerable amount of time. It is initially necessary, using wet analysis, to withdraw samples from the product streams and to process these samples appropriately (drying, grinding, homogenizing, etc.) before analysis can begin. In such wet chemical analysis methods, a time delay of several hours, even up to a day, can be expected from the taking of the sample to the result of analysis. This can mean that entire daily productions will have to be discarded.

Time-consuming wet chemical analysis is, in part, being replaced by X-ray fluorescence analysis. In this method, use is made of dispersive, conventional multichannel X-ray spectrometers with excitation by an X-ray tube. To their disadvantage, use of these devices involves a time delay between the taking of the sample and the analytical result, caused by the necessary preparation of the sample, even though a substantial saving in time is obtained as compared with wet chemical analysis.

In order to reduce the time delay occurring with these processes between the taking of the sample and the analytical result, devices and processes have been developed making it possible to carry out a direct analysis at the product stream. In this context, mention can be made of the on-stream analysis system Courier 300 developed by the company Outokumpu Oy of Finland. This device is, in principle, a continuously operating sample-taking system with discontinuous analysis based on X-ray fluorescence. In this process, a partial product stream is conducted from various sample-taking points in the flotation plant, via pumps and pipelines, to a battery of measuring cells. A movable measuring head with X-ray tube and analytical section travels at predetermined time intervals along the various cells and thus determines, in a quasi-continuous fashion, the elemental contents of the individual slurry streams. Since this arrangement is very expensive, it can hardly be considered for use in relatively small flotation plants.

So-called immersion probes have also been developed. In contrast to the conventional X-ray fluorescence method, these devices utilize, in place of excitation by an X-ray tube, excitation by an isotope source. The immersion probes are hung in the slurry stream, and in case of flotation plants, for example, in the so-called flotation cells. One disadvantage here is the inhomogeneity of the slurry usual in flotation cells. Further, an additional density measuring probe is necessary in all cases. Such immersion probes have been developed by the companies Outokumpu Oy of Finland, Philips of Australia, and NUTMAQ of England.

All of the on-line analysis devices heretofore developed on the basis of X-ray fluorescence initially determine the element content of the slurry. The determination of the element content in the solid matter is possible only by means of an additionally required measurement of the slurry density. Since densimeters, however, operate precisely only in a bicomponent system of liquid/solid matter, the results can be greatly falsified, for example, by air occlusions in the slurry, which can be expected in flotation processes. This fact must be considered a decisive disadvantage of the conventional XRFA processes.

In addition to the devices operating on the basis of X-ray fluorescence, attention must also be drawn to on-line analysis devices operating according to the principle of neutron activation analysis. In these devices, a partial slurry stream flows continuously first through an irradiation cell with the neutron source. Here the slurry is "activated" and then flows via an inductive flowmeter into a measuring cell provided with a detector, where the induced activity is measured. During backflow, the slurry passes a densimeter. Thus, neutron activation analysis devices absolutely require a density measurement. Furthermore, a specific slurry through-flow, constant at all times, must be maintained.

SUMMARY OF THE INVENTION

It is an object of the present invention to provide a process and apparatus for the rapid, continuous element analysis of process streams.

It is a further object of the present invention to provide a process and apparatus for the determination of element concentrations in slurry streams which is independent of slurry density and composition.

Additional objects and advantages of the present invention will be set forth in part in the description which follows and in part will be obvious from the description or can be learned by practice of the invention. The objects and advantages are achieved by means of the processes, instrumentalities and combinations particularly pointed out in the appended claims.

To achieve these objects, and in view of its purpose, the present invention provides a process for the continuous measurement, by X-ray fluorescence analysis, of the element content of a slurry, independently of the slurry density and slurry composition, comprising: (a) passing a sample of the slurry to be measured between an excitation source of primary radiation and a detector, with a target being arranged between the source and the sample so that (1) a portion of the source radiation excites the target to emit a target radiation which penetrates the sample and then is absorbed by the detector, (2) a portion of the source radiation penetrates the sample and excites the element in the slurry which is to be measured to emit elemental X-ray radiation which is then absorbed by the detector, and (3) a portion of the source radiation penetrates and passes through the sample and is absorbed by the detector; and (b) evaluating the radiation absorbed by the detector to directly determine the elemental content of the sample.

The radiation absorbed by the detector defines a spectrum, and the evaluation of the radiation preferably comprises determining the net peak area of the spectrum for the elemental radiation by three channel integral evaluation.

The present invention also provides an apparatus for the continuous measurement, by X-ray fluorescence analysis, of the elemental content of a slurry, independently of slurry density and slurry composition, comprising: (a) a measuring chamber having a slurry flow duct, a first measuring window at one side of the measuring chamber, and a second measuring window at an opposite side of the measuring chamber, (b) an excitation source of primary radiation externally of the measuring chamber on the side with the first window and aligned with the first and second measuring windows, (c) a target located between the source and the first measuring window, and (d) a radiation detector externally of the measuring chamber on the side with the second window, and aligned with the first and second windows, the excitation source, the measuring chamber and the detector being arranged such that primary radiation penetrates the chamber and strikes the detector, and the target being arranged such that primary radiation excites the target to emit target radiation which penetrates the measuring chamber and strikes the detector.

It is to be understood that both the foregoing general description and the following detailed description are exemplary, but are not restrictive of the invention.

BRIEF DESCRIPTION OF THE DRAWINGS

The accompanying drawings, in which like numbers indicate like parts, illustrate examples of presently preferred embodiments of the invention and, together with the description, serve to explain the principles of the invention.

DETAILED DESCRIPTION OF THE INVENTION

In the process of the present invention, the slurry stream to be analyzed continuously passes through an agitated vessel. In this vessel, the slurry is homogenized, and it is thereby possible to take from the slurry stream a sample in the form of a representative partial slurry stream. The partial stream is conducted by means of a pump through a measuring chamber installed in the pump delivery line and is reintroduced into the agitated vessel and/or into the exciting primary slurry stream. The measuring chamber comprises a slurry flow channel and two measuring windows, one on each side of the slurry flow channel. A radioactive excitation source is arranged laterally of one of the measuring windows at the measuring chamber and a detector is arranged laterally of the other measuring window. The excitation source emits a primary radiation $J_o$. A part of this primary radiation excites in a target (e.g. Ag foil), arranged between the excitation source and the slurry flow channel, the X-ray radiation $J_1$ of the target. The target radiation penetrates the slurry and is absorbed by the detector. Another part of this primary radiation excites the X-ray radiation $J_f$ of the element to be analyzed in the slurry. In the detector, the primary radiation, weakened by the slurry in the measuring chamber, the target radiation, also weakened by the slurry in the measuring chamber, and the elemental X-ray radiation, also weakened by the slurry in the measuring chamber, are recorded and converted in the electric impulses. After passing through a preamplifier and a main amplifier, as well as a spectrum enhancer, these impulses are fed to a multichannel analyzer. This analyzer transmits the integrals of regions of the spectrum of interest to an evaluating unit.

The XRFA measuring procedure thus developed makes it possible to effect the simultaneous measurement of primary variables (X-ray lines) as well as auxiliary variables, such as transmission or scattering. The determination of the concentration of a desired element thereby becomes independent of the slurry density and the slurry composition. In contrast to generally utilized reflective measurement geometries, a transmission geometry is employed in the present method, in which the sample to be measured is placed between the excitation source and the detector. This measuring arrangement permits the recording not only of the X-ray lines excited in the sample, but also of the primary radiation transmitted through the sample and of the X-ray radiation excited in a target and transmitted through the sample. By varying the measuring chamber geometry, especially the layer thickness of the slurry stream between the measuring windows in the slurry flow channel, various element systems can be optimally analyzed. In the present invention, a novel spectrum-evaluating method is utilized, making it possible to conduct evaluation and calculation of concentration with the use of small table-top computers.

The analyzing apparatus according to the present invention is designed to be movable and thus can be utilized during operation selectively at various, strategically important slurry streams. Even in the case of a flow of the slurry which is accessible only with difficulty, such as, for example, in flotation plants for processing of mineral raw materials where the slurry often can be reached only from the so-called "leakage floor", it is possible, for example, by a separate arrangement of the slurry pump, to adapt the slurry cycle, even in such a case, to the local conditions.

The apparatus of the present invention makes it possible to effect a continuous measurement of element contents in the slurry, independently of the slurry density and the slurry composition. Falsifications of analytical results by air occlusions in the slurry, frequently present in flotation processes, are excluded. Furthermore, there is no need for an expensive electronic measuring and evaluating circuitry. Thus, simple operation and low susceptibility to trouble are attained by practice of the present invention.

Figure 1:
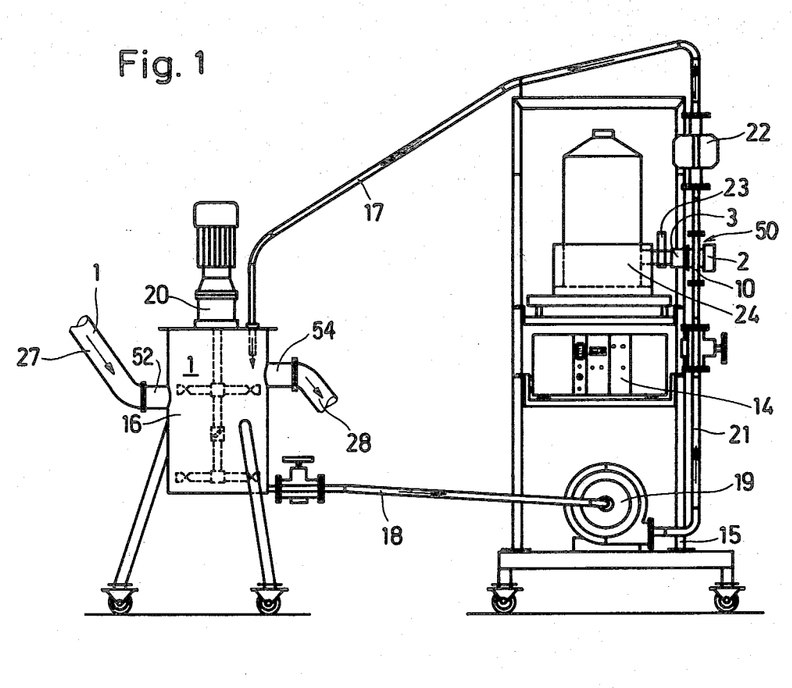
FIG. 1 shows one embodiment of a measuring unit and an agitator equipped vessel which can be used in the practice of the present invention.

Referring now to the drawings, the apparatus, as shown in FIG. 1, comprises a measuring unit, generally 50, of compact construction, the individual parts of which are arranged in a frame 15, and of an agitator-equipped vessel 16. Both parts of the apparatus are designed to be movable and are connected to each other by flexible conduits in the form of an intake line 18 of a pump 19 and a delivery line 17 of pump 19. In the case of slurry conduits which are accessible only with difficulty and can be reached often only from the so-called flotation leakage floor, there is the possibility even here to adapt the slurry circulation to the local conditions, for example, by a separate arrangement of slurry pump 19. The analyzer can thus be employed at various locations of an industrial plant.

Agitated vessel 16 is equipped with an agitator unit 20 provided with countercurrent stirrers. Agitated vessel 16 serves for homogenizing a slurry stream 1 to be analyzed. An inlet connecting piece 52 is attached to agitated vessel 16 for connecting vessel 16 to a feed pipe 27 for the slurry. Similarly, a discharge connecting piece 54 is attached to agitated vessel 16 for connecting vessel 16 to a discharge pipe 28 for the slurry.

The measuring unit comprises a frame 15 wherein the individual units required for the measurement are installed. These units comprise a slurry pump 19 with infinitely variable speed control, a measuring chamber 10 and an inductive flowmeter 22. Measuring chamber 10 and inductive flowmeter 22 are arranged in a pressure delivery line 21 of slurry pump 19.

Inductive flowmeter 22, shown in FIG. 1, serves basically only for early recognition of disturbances in the slurry circulation. It has been found that the analytical method proper operates to a great degree independently of the flow rate.

A Si (Li) detector 3 with a preamplifier 23 and a cryostat 24 is arranged opposite a radioactive source 2, flanged to measuring chamber 10, in a mounting which is adjustable in all directions. Parts of an electronic measuring circuit 14, such as high-voltage supply, main amplifier, and spectrum enhancer, are accommodated in frame 15. Since the monitoring of a process takes place in industry in most cases from a central control point, the electronic evaluating circuitry, such as the multichannel analyzer, the computer, and the read-out device, have not been incorporated into the compact system shown in the drawings.

Flotation slurries involve in most cases abrasive media. For this reason, the analyzer preferably is provided with a centrifugal pump 19 equipped with a wear-resistant pump. Also, a so-called dry seal preferably is used with respect to the shaft sealing means, since during calibration tests in the laboratory, the water-solid ratio of the slurry 1 is not supposed to be altered by incoming seal flushing water.

Figure 2:
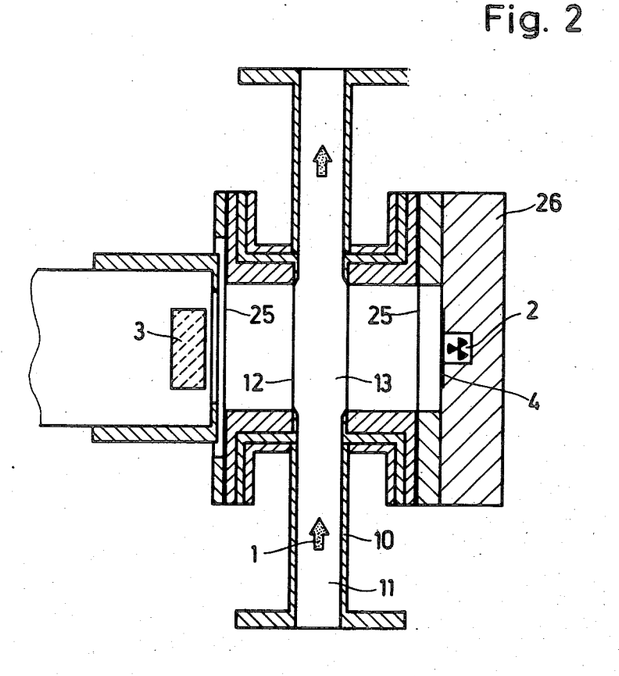
FIG. 2 is a cross-sectional view of one embodiment of a measuring chamber which can be used in the present invention.

Measuring chamber 10, as shown in FIG. 2, consists essentially of a rectangular slurry flow duct or channel 11, the cross section of which is adapted to the slurry 1 to be analyzed. Measuring windows 12 and 13, made of a 300 $\mu m$ thick "Hostaphan" terephthalate (Hoechst AG) film, necessary in XRFA processes, are mounted on both sides of flow duct 11. These window films 12 and 13 cannot be chosen to be of any desired thickness, but must be sufficiently thick such as 300 $\mu m$, for reasons of radiation absorption, and are subject to constant wear since they come directly into contact with slurry stream 1. This factor can, in the end, lead to a destruction of films 12 and 13. To prevent any slurry from exiting if this should happen, measuring chamber 10 is provided on both sides with an additional protective film (Hostaphan) 25. On the side of measuring chamber 10 facing away from dector 3, an excitation source 2 of radioactivity is mounted, together with an appropriate source shield 26. A target 4 is provided for source 2 between slurry flow duct 11 and source 2. As can be seen in FIG. 2, source 2, target 4, measuring windows 12 and 13 and detector 3 are laterally aligned with each other. The source and target materials are selected as a function of the elements to be determined in the slurry.

Slurry stream 1 to be analyzed passes continuously through agitator equipped vessel 16 of FIG. 1, in which it is homogenized. It is thereby possible to withdraw from the slurry stream a representative partial slurry stream 18 through conduits 18, 21 and 17. The partial stream is conducted by means of pump 19 through measuring chamber 10 installed in pump delivery line 21 and reintroduced into agitated vessel 16 and/or into the main slurry stream being discharged.

Figure 3:
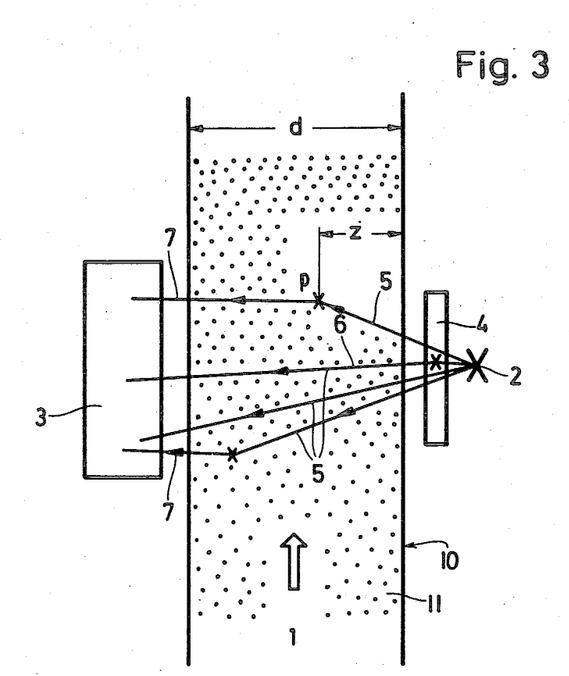
FIG. 3 is a schematic representation of the path of the radiation through a measuring chamber in accordance with the present invention.

As can be seen in FIG. 3, radioactive source 2 is arranged laterally at measuring chamber 10 and emits a primary radiation $I_o$, shown by reference numeral 5 in FIG. 3. A portion of this primary radiation 5 excites in target 4 (e.g., an Ag foil) X-ray radiation $I_1$, shown by reference numeral 6, of target 4, and another portion of the primary radiation 5 excites the X-ray radiation $I_f$, shown by reference numeral 7, of the element to be analyzed in the slurry. In detector 3, the primary, target, and elemental X-ray radiations 5, 6, and 7, weakened by slurry 1 in the measuring chamber 10, are registered and converted into electrical impulses. After passing through the preamplifier and main amplifier, as well as the spectrum enhancer, these impulses are applied to a multichannel analyzer, which is a part of electronic circuit 14, shown in FIG. 1. The analyzer determines the integrals of regions of interest of the spectrum and feeds this information to the evaluating units.

The theoretical basis of the present method of analysis will now be discussed.

The intensity $dJ_f$ of the X-ray radiation 7 excited in an elemental volume (around the point p shown in FIG. 3) of a sample 1 of slurry can be expressed as follows:

$$dJ_{fp} = K'_f \rho_p \cdot ds \cdot dz \cdot C_p \cdot \exp(-\mu_{op} \cdot \rho_p \cdot z) \qquad (1)$$

where $K'_f$ indicates the yield of characteristic X-ray radiation of the desired element, as well as the geometrical factor and the absorption of the primary radiation 5 in the space between source 2 and the boundaries of the sample, and $\rho_p$ is sample density, ds·dz is the elemental volume, $C_p$ is the concentration of the desired element in the sample, $\mu_{op}$ is the mass absorption coefficient of the sample for the primary radiation (index o), and z is the path of the primary radiation in the sample up to excitation of the X-ray radiation. (See FIG. 3 for "z")

I is a intensity at any point between the source and the detector

J is the intensity registered at the detector

The excited elemental X-ray radiation 7 is weakened in sample 1 along the distance "d-z" by the factor:

$$\exp(-\mu_{fp}\rho_p(d-z))$$

The radiation absorption in the space after the sample 1 is treated as a constant.

The symbol "d" indicates the sample thickness (thickness of the measuring chamber duct 11), as can be see in FIG. 3. Detector 3 records the intensity $J_f$ of the fluorescent X-ray radiation 7 excited in the elemental volume of sample 1:

$$J_f = \int_V \exp(-\mu_{fp} \cdot \rho_p \cdot (d-z)) \cdot dJ_{fp} \qquad (2)$$

In this connection, "V" means the sample volume to be covered by detector 3. The integration of Equation (2), taking into account Equation 1, yields:

$$J_f = K''_f \frac{C_p}{\mu_{op} - \mu_{fp}} [\exp(-\mu_{fp} \cdot \rho_p \cdot d) - \exp(-\mu_{op} \cdot \rho_p \cdot d)] \qquad (3)$$

The constant $K''_f$ contains $K'_f$, as well as the other constants stemming from the integration.

The concentration "C" of the element to be determined in the solid matter is correlated with $C_p$ by the following formula:

$$C_p = C \cdot \frac{1 - \dfrac{\rho_W}{\rho_p}}{1 - \dfrac{\rho_W}{\rho_F}} \qquad (4)$$

Where $\rho_W$ and $\rho_F$ are the densities of the water (index W) and of solid matter (index F), respectively.

Furthermore, it is to be considered that the following applies:

$$\mu_{op} = (\mu_{oF} - \mu_{oW}) \cdot C_F + \mu_{oW} \qquad (5)$$

$$\mu_{fp} = (\mu_{fF} - \mu_{fW}) \cdot C_F + \mu_{fW}$$

The concentration of the solid matter in the slurry is designated by $C_F$, and the following applies:

$$C_p = C_F \cdot C$$

The mass absorption coefficients of the solid and of the water for primary radiation (index o) and fluorescent (index f) radiation are denoted by $\mu_{oF}$ and $\mu_{oW}$ and as $\mu_{fF}$ and $\mu_{fW}$, respectively. In this connection, one must take into account that the coefficients $\mu_{oF}$ and $\mu_{fF}$ are dependent on the chemical composition of the solid:

$$\mu_{iF} = (\mu_{iE} - \mu_{iM}) \cdot C + \mu_{iM} \qquad (6)$$

where "i" refers to the primary (i=o) or the fluorescent (i=f) radiation, respectively.

Symbols $\mu_{iE}$ and $\mu_{iM}$ denote the mass absorption coefficients of the element (E) to be determined and of the solid matrix (M).

The portion of primary radiation 5 registered by detector 3 can be expressed by the following, known equation:

$$J_{To} = K_{To} \cdot \exp(-\mu_{op} \cdot \rho_p \cdot d) \qquad (7)$$

In this context, $K_{To}$ is to be interpreted as a constant of the apparatus ($u_{op} \cdot \rho_p = 0$). This equation immediately permits the replacement of the member $\exp(-u_{op} \cdot \rho_p \cdot d)$ in Formula (3) by a measurable variable $J_{To}/K_{To}$.

The member "$\exp(-u_{fp}\rho_p d)$" can be determined in a similar way. However, in this case, the transmission of another proximate line must be measured in place of the transmission of the X-ray fluorescence line.

To obtain this line, a target 4 is employed, the X-ray line of which is close to that of the desired element, but yet can be measured separately by means of the detector 3 employed. In this case, the following applies:

$$J_{T1} = K_{T1} \cdot \exp(-\mu_{1p} \cdot \rho_p \cdot d) \qquad (8)$$

Here, the energy of the X-ray line of the target 4 bears the index "1" and $J_{T1}$ is the portion of the target radiation 6 registered by detector 3.

If energy "1" is close to energy "f", and also lies below the absorption edge of the desired element, the following approximation can be utilized:

$$\mu_{fp} = r \cdot \mu_{1p} \qquad (9)$$

PS where the factor "r" represents a constant to be determined.

The combination of Equations (3), (8), and (9) yields:

$$J_f = K''_f \cdot \frac{C_p}{\mu_{op} - \mu_{fp}} \left[ \left(\frac{J_{T1}}{K_{T1}}\right)^r - \frac{J_{To}}{K_{To}} \right] \qquad (10)$$

With the aid of Equations (7), (8), and (9), the following equations are similarly obtained:

$$\mu_{op} = \frac{L_0}{\rho_p \cdot d}, \; \mu_{fp} = \frac{r \cdot L_1}{\rho_p \cdot d} \qquad (11)$$

where:

$$L_0 = L_n \frac{K_{To}}{J_{To}}, \; L_1 = L_n \frac{K_{T1}}{J_{T1}}$$

Equation (10) now will look as follows:

$$J_f = K''_f \cdot \frac{C_p \cdot \rho_p \cdot d}{L_0 - r \cdot L_1} \cdot \left[ \left( \frac{J_{T1}}{K_{T1}} \right)^r - \frac{J_{T0}}{K_{T0}} \right] \quad (12)$$

The following is obtained from Equation (4), considering that $C_p = C \cdot C_F$:

$$C_p \cdot \rho_p \cdot d = \frac{C \cdot \rho_w \cdot d}{\frac{1}{C_F} - \left( 1 - \frac{\rho_W}{\rho_F} \right)} \quad (13)$$

A combination of Equations (4), (5), and (11) leads to:

$$\frac{1}{C_F} - \left( 1 - \frac{\rho_W}{\rho_F} \right) = \left( \frac{\mu_{oF}}{\mu_{oW}} - \frac{\rho_W}{\rho_F} \right) \cdot \frac{\mu_{oW} \cdot \rho_W \cdot d}{L_0 - \mu_{oW} \cdot \rho_W \cdot d} \quad (14)$$

Formula (12) can now be rewritten without the appearance of the slurry density:

$$J_f = K''_f \cdot \frac{C \cdot (L_0 - \mu_{oW} \cdot \rho_W \cdot d)}{\left( \frac{\mu_{oF}}{\mu_{oW}} - \frac{\rho_W}{\rho_F} \right) \cdot \mu_{oW}} \cdot \frac{\left( \frac{J_{T1}}{K_{T1}} \right)^r - \frac{J_{T0}}{K_{T0}}}{L_0 - r \cdot L_1} \quad (15)$$

In this connection, Equation (6) must be furthermore considered with respect to $\mu_{oF}$:

$$\mu_{oF} = (\mu_{oE} - \mu_{oM}) \cdot C + \mu_{oM}$$

This leads to:

$$J_f = K''_f \cdot \frac{C}{(\mu_{oE} - \mu_{oM}) \cdot C + \mu_{oM} - \mu_{oW} \cdot \frac{\rho_W}{\rho_F}} \cdot \quad (16)$$

$$\frac{L_0 - \mu_{oW} \cdot \rho_W \cdot d}{L_0 - r \cdot L_1} \cdot \left[ \left( \frac{J_{T1}}{K_{T1}} \right)^r - \frac{J_{T0}}{K_{T0}} \right]$$

This Equation (16) expresses the dependency between the concentration C to be determined and the measuring variables $J_f$, $J_{T0}$, $J_{T1}$. Only a strong variation in the chemical composition of the solid matrix can, due to changes in $\mu_{oM}$ and $\rho_F$, lead to errors in the determination of concentration C.

To determine the constant parameters in Formula (16) empirically, an additional conversion must be carried out. The following designations or abbreviations are to be introduced:

$$x = L_0 - r \cdot L_1 = K_{01} + L_{01} \quad p = \mu_{oE} - \mu_{oM}$$

$$L_{01} = Ln \frac{J_{T1}}{J_{T0}}, \quad K_{01} = Ln \frac{K_{T0}}{K'_{T1}} \quad q = \mu_{oM} - \mu_{oW} \cdot \frac{\rho_W}{\rho_F}$$

$$K'_{T0} = K_{T0} \cdot \exp(-\mu_{oW} \cdot \rho_W \cdot d) \quad K = \frac{K''_f}{K_{T0}}$$

$$L'_0 = Ln \frac{K'_{T0}}{J_{T0}}$$

At this point, Equation (16) can be written as follows:

$$J_f = K \cdot \frac{C}{p \cdot C + q} \cdot L'_0 \cdot J_{T0} \cdot \frac{e^x - 1}{x} \quad (17)$$

or $$\frac{1}{C} = -\frac{p}{q} + \frac{K}{q} \cdot \frac{J_{T0}}{J_f} \cdot L'_0 \cdot \frac{e^x - 1}{x} \quad (18)$$

The use of Taylor's expansion results in:

$$\frac{e^x - 1}{x} = 1 + \frac{x}{2!} + \frac{x^2}{3!} + \frac{x^3}{4!} + \ldots \quad (19)$$

$$= a_1 + a_2 \cdot L_{01} + a_3 \cdot L_{01}^2 + a_4 \cdot L_{01}^3 + \ldots$$

where $$a_1 = 1 + \frac{K_{01}}{2!} + \frac{K_{01}^2}{3!} + \ldots$$

$$a_2 = \frac{1}{2!} + 2 \cdot \frac{K_{01}}{3!} + 3 \cdot \frac{K_{01}^2}{4!} + \ldots$$

$$a_3 = \frac{1}{3!} + 3 \cdot \frac{K_{01}}{4!} + 4 \cdot \frac{K_{01}^2}{5!} + \ldots$$

etc.

This makes it possible to represent Equation (18) with the following series expansion:

$$1/C = A_0 + A_1 \cdot x_1 + A_2 \cdot x_2 + A_3 \cdot x_3 \ldots \quad (20)$$

where:

$$A_0 = -\frac{p}{q}$$

$$A_1 = \frac{K}{q} \cdot A_1$$

$$A_2 = \frac{K}{q} \cdot A_2 \text{ etc.}$$

$$x_1 = \frac{J_{T0}}{J_f} \cdot L'_0$$

$$x_{i+1} = x_i \cdot L_{01} \text{ for } i \geq 1$$

Equation (20) is linear with respect to unknown coefficients $A_o$, $A_1$, $A_2$,—With the aid of a measuring series on samples having varying, but known concentrations C and arbitrary densities, which densities cover the range of interest, these coefficients can be determined by means of multiple linear regression.

Starting values for the constants "r" and "$K'_{T_0}$" necessary in the calculation of $x_1$ may be estimated theoretically (r) or empirically ($K'_{T_0}$). These values are then modified stepwise in the direction toward an improved value for the multiple regression coefficient (or for $x^2$). This procedure is repeated by computer until the maximum has been reached for the regression coefficient or until the minimum has been reached for the $x^2$ value. An optimum regression degree (the highest "i") is found in accordance with the same criteria.

The present invention will now be described using as an example the determination of $BaSO_4$ in a fluospar ($CaF_2$) slurry concentrate, at various concentrations between 0 and 5%. To determine BaSO4, the source 2 is provided as Am-241. The BaSO4 analysis procedure requires that X-ray K-lines of silver be obtained, and to do this target 4 is provided as a silver foil.

The Am-241 radioactive source 2 emits a primary radiation $I_o$, shown by reference numeral 5. A portion of this primary radiation 5 excites in the Ag target 4 an X-ray radiation $I_1$, shown by reference numeral 6, of target 4, and another portion of the primary radiation 5 excites the X-ray radiation $I_f$, shown by reference numeral 7 of the element Ba to be analyzed in the slurry. In detector 3, the primary, target, and elemental X-ray radiations 5, 6, and 7 for the BaSO4 determination, weakened by slurry 1 in the measuring chamber 10, are registered and converted into electrical impulses. After passing through the preamplifier and main amplifier, as well as the spectrum enhancer, these impulses are applied to a multichannel analyzer, which is a part of electronic circuit 14, shown in FIG. 1, such as a three channel integral analyzer. The analyzer determines the integrals of spectrum ranges of interest, corresponding to the net areas of the peaks representing various elements, and feeds this information to the evaluating unit.

Figure 4:
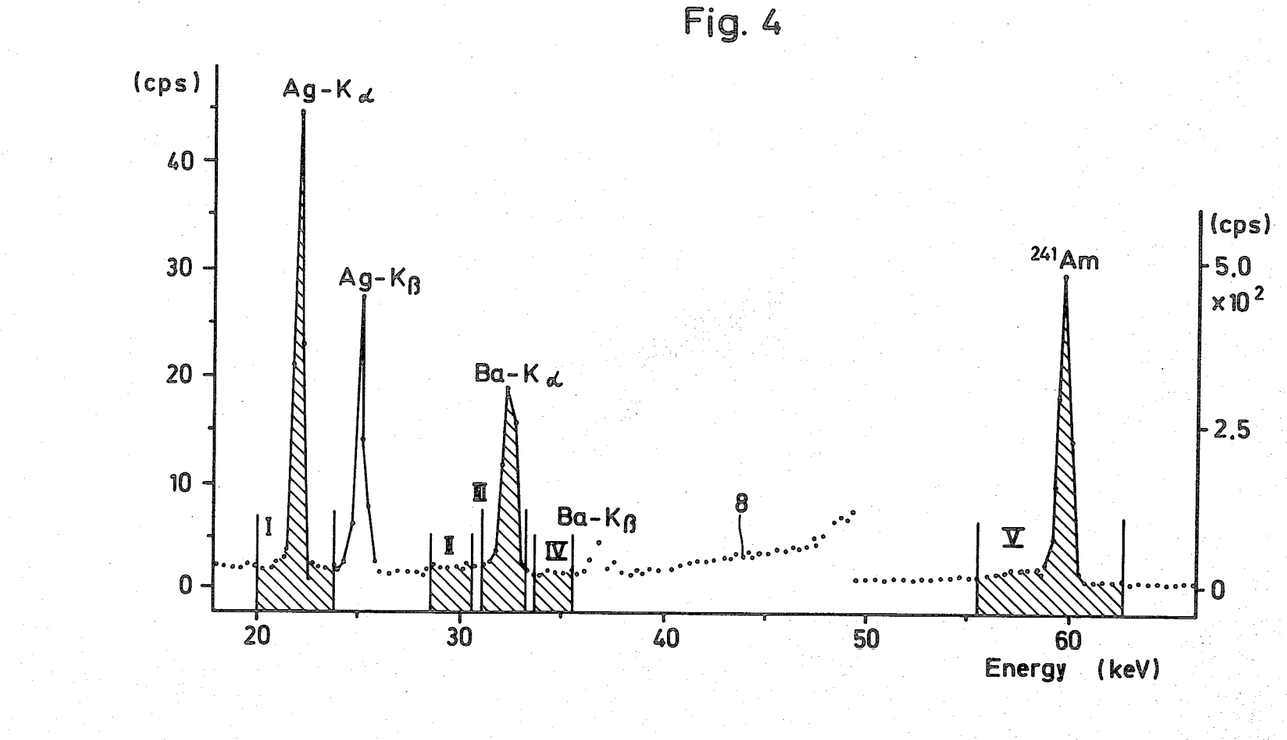
FIG. 4 shows an X-ray fluorescence analysis spectrum of a $CaF_2$ slurry which contains 3% $BaSO_4$, produced according to the present invention.
Figure 5:
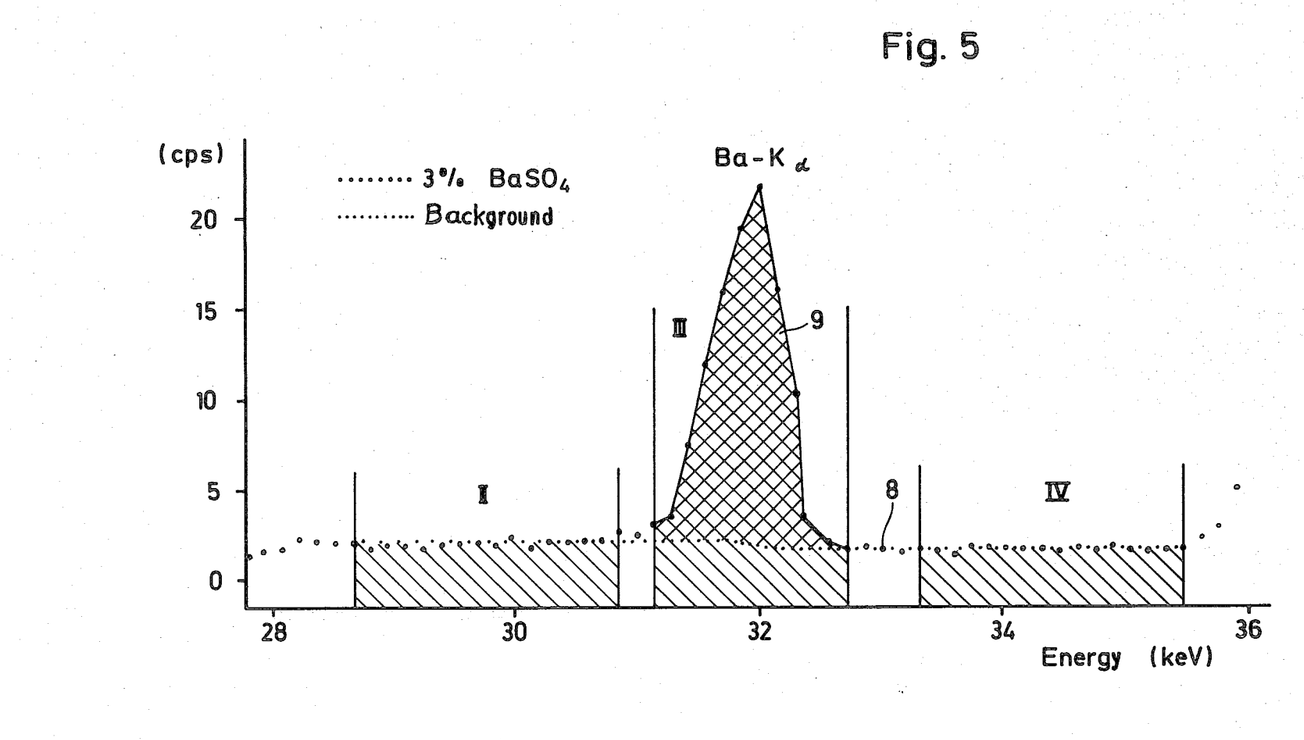
FIG. 5 is an enlarged view of a portion of the spectrum of FIG. 4.

The peaks representing the elements Ag, Ba and Am are shown in FIGS. 4 and 5 for a particular determination. In particular, the XRFA spectrum of a CaF2 slurry which contains 3% BaSO4 is shown in FIG. 4 where the background is represented by dotted line 8. An enlarged view of a portion of the spectrum of FIG. 4 for determining the net peak area of Ba-$K_\alpha$ for a BaSO4 concentration of 3%, using a radiation source of 10 mC Am-241, with an Ag target, a Si(Li)/100 sec. detector and a slurry density of 1.2 g/cm$^3$ is shown in FIG. 5. Background 8 (dotted line, simple shading) in zone III, in which zone the Ba-$K_\alpha$ line appears, is determined by evaluating the background of the two secondary areas II and IV which are adjacent to zone III. Peak area 9, shown in FIG. 5 by cross-hatching, corresponds to the net peak area of Ba-$K_\alpha$ for this determination ($K_\alpha$ is the first line of the K-serie).

Figure 6:
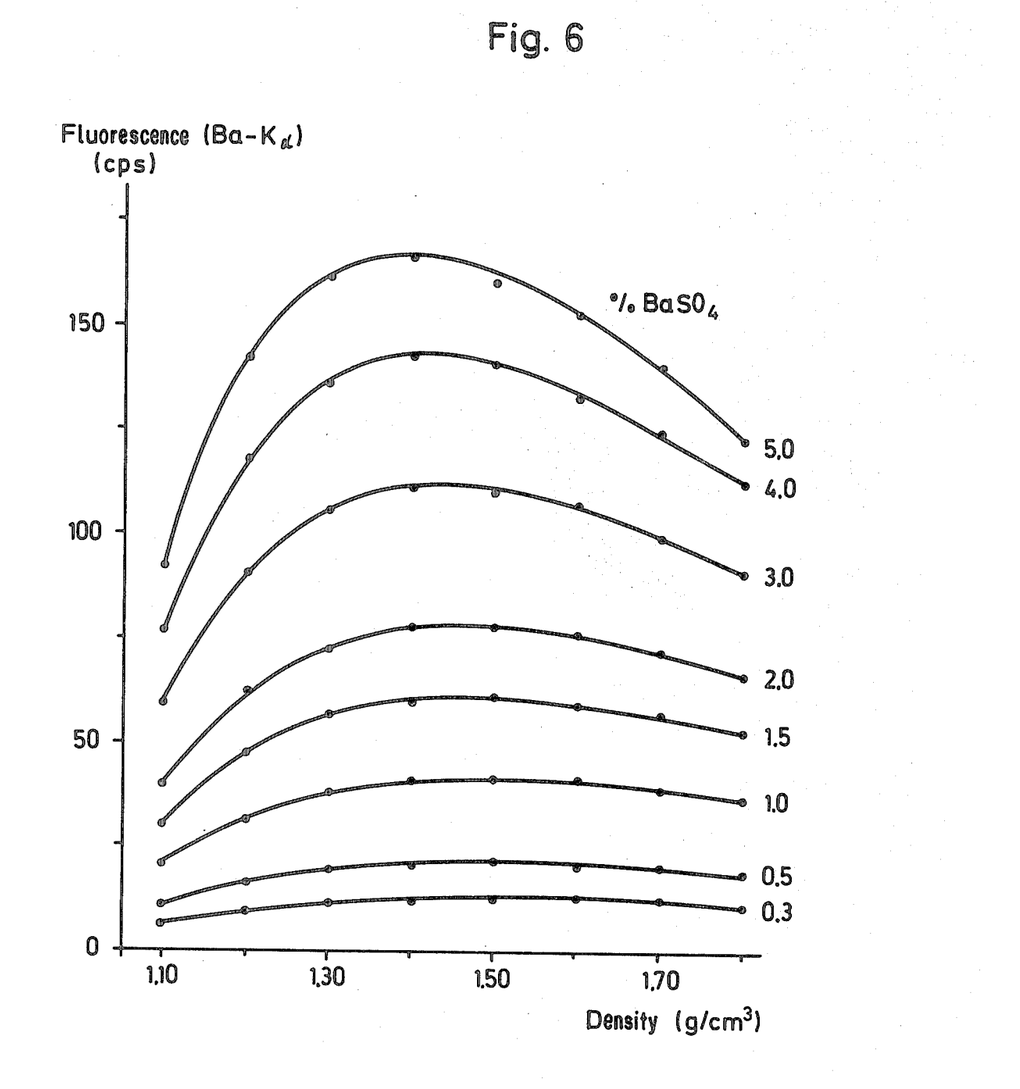
FIG. 6 is a plot of fluorescence vs. slurry density for various concentrations of $BaSO_4$, made according to the present invention.

FIG. 6 represents a plot of fluorescence vs. slurry density for various concentrations of BaSO4, from 0 to 5%.

It is important to registrate in the detector 3 so high intensity $J_f$(see eq (3)) as possible for a given concentration range of the element to be determined and for a particular slurry 1 using the condition: $(\partial J_f/\partial d)=0$. Thus with the aid of equation (3) the following formula is obtained.

$$d = \frac{\ln \frac{\mu_{fp}}{\mu_{op}}}{\rho_p \cdot (\mu_{fp} - \mu_{op})}$$

Figure 7:
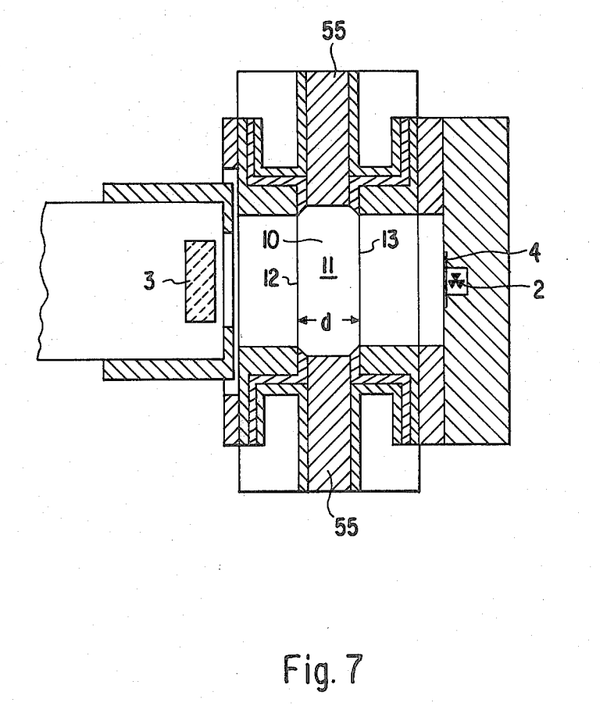
FIG. 7 represents a cross-sectional view of the measuring chamber with spacing-strips for varrying the cross-sectional area of the measuring chamber (90° rotated to FIG. 2).

The cross-sectional area can be varied in the way shown in FIG. 7 with proper spacing-strips 55.

The set of coefficients $A_o$ to $A_n$, "r", "$K_{To}$" which corresponds to the minimum of x$^2$-value by the optimal degree of regression "n" becomes to be the calibration set of coefficients for determining any unknown concentration in that particular system.

The evaluation of a sample with an unknown concentration follows the way:

(a) A XRFA spectrum of an unknown sample should be measured.

(b) The intensities $J_f$, $J_{To}$ and $J_{T1}$ should be evaluated from this spectrum.

(c) The unknown concentration should be evaluated using the calibration coefficients set and a simple inversion of the formula (20) page 22, line 8:

$$C=[A_o+A_1 \cdot x_1 + A_2 \cdot x_2 + - + A_n \cdot x_n^{-1}] \tag{21}$$

Examples for

| Elements | source | target |
|---|---|---|
| Pb | $^{57}$Co, $^{109}$Cd | Hg, Au |
| W | $^{57}$Co, $^{109}$Cd | Hf |
| Sn | $^{241}$Am, $^{153}$Gd | Rh |
| Ag | $^{241}$Am, $^{153}$Gd | Mo |
| Ba | $^{241}$Am | Ag |

For multiple linear regression may be used any computer like PDP 11/34 from Digital Equipment.

For "on-line" processing it is enough to use a programmable desk-calculator like HP-97.

| Electronic: | | |
|---|---|---|
| X-Ray Amplifier | 1713 | Canberra Industries |
| Spectrum enhancer | 1764 A | " |
| Multichannelanalyser | 1056 | UNICOM GmbH |
| BCD-Interface for HP-97 | PI 97 A | D. WIELAND GmbH |

The programming of multiple linear regression is handled in many handbooks about data processing for example:

C. Daniel, F. S. Wood: "Fitting equations to data", WILEY-Interscience, 1971

B. W. Arden, K. N. Astill: "Numerical algorithms", Addison-Wesley publishing company, 1970.

User's Manuell for HP-97 desk-calculator may be helpful to explain how to programme the equations like (21).

It will be understood that the above description of the present invention is susceptible to various modifications, changes and adaptations, and the same are intended to be comprehended within the meaning and range of equivalents of the appended claims.

What is claimed is:

1. A process for the continuous measurement, by X-ray fluorescence analysis, of the element content of a slurry, independently of the slurry density and slurry composition comprising:

(a) passing a sample of the slurry to be measured between an excitation source of primary radiation and a detector, with a target being arranged between the source and the sample so that (1) a portion of the source radiation excites the target to emit a target radiation which penetrates the sample and then is absorbed by the detector, (2) a portion of the source radiation penetrates the sample and excites in the slurry among other elements the element which is to be measured to emit elemental X-ray radiation which is then absorbed by the detector, and (3) a portion of the source radiation penetrates and passes through the sample and is absorbed by the detector; and (b) evaluating the radiation absorbed by the detector to directly determine the elemental content of the sample.

2. The process according to claim 1, wherein the radiation absorbed by the detector defines a spectrum, and the evaluation of the radiation comprises determining the net peak area of the spectrum for the elemental radiation by three channel integral evaluation.

3. An apparatus for the continuous measurement, by X-ray fluorescence analysis, of the elemental content of a slurry, independently of slurry density and slurry composition, comprising:
- (a) a measuring chamber having a slurry flow duct, a first measuring window at one side of the measuring chamber, and a second measuring window at an opposite side of the measuring chamber;
- (b) an excitation source of primary radiation externally of the measuring chamber on the side with the first window and aligned with the first and second measuring windows;
- (c) a target located between th source and the first measuring window, the excitation source providing a primary radiation a portion of which can pass through the slurry and the target, and a portion of which can excite in the slurry among other elements the element which is to be measured to emit elemental x-ray radiation; and
- (d) a radiation detector externally of the measuring chamber on the side with the second window and aligned with the first and second windows, with the excitation source, the measuring chamber and the detector being arranged such that (1) primary radiation penetrates the chamber and strikes the detector and (2) primary radiation excites in the slurry the element which is to be measured to emit elemental x-ray radiation from the slurry which elemental x-ray radiation strikes the detector, and the target being arranged such that primary radiation excites the target to emit target radiation which penetrates the measuring chamber and strikes the detector, to enable the determination of the element content.

4. Apparatus according to claim 1 including means to vary the cross-sectional area of the slurry flow duct.

5. Apparatus according to claim 3 additionally comprising electronic apparatus for evaluation of radiation which strikes the detector.

6. Apparatus according to claim 4 wherein the electronic apparatus comprises a multi-channel integral evaluator.

7. Apparatus according to claim 3 wherein the source of primary radiation is Am-241, the target is silver foil, and the detector is a Si(Li) detector.

8. Apparatus according to claim 3 wherein the detector is an electrical circuit having an electronic evaluating circuit.

9. The process according to claim 1, wherein the excitation source of primary radiation is provided by a material selected from the group consisting of $^{57}$Co, $^{109}$Cd, $^{241}$Am and $^{153}$Gd.

10. The apparatus according to claim 3, wherein the excitation source of primary radiation is provided by a material selected from the group consisting of $^{57}$Co, $^{109}$Cd, $^{241}$Am and $^{153}$Gd.

11. The process according to claim 1, wherein the target has an ordinal which is at least one unit lower than the element to be determined.

12. The process according to claim 1, wherein the element to be determined is Pb and the target is Hg or Au.

13. The process according to claim 1, wherein the element to be determined is Cd and the target is Hf.

14. The process according to claim 1, wherein the element to be determined is Sn and the target is Rh.

15. The process according to claim 1, wherein the element to be determined is Ag and the target is Mo.

16. The process according to claim 1, wherein the element to be determined is Ba and the target is Ag.

17. The apparatus according to claim 3, wherein the element to be determined is Pb and the target is Hg or Au.

18. The apparatus according to claim 3, wherein the element to be determined is Cd and the target is Hf.

19. The apparatus according to claim 3, wherein the element to be determined is Sn and the target is Rh.

20. The apparatus according to claim 3, wherein the element to be determined is Ag and the target is Mo.

21. The process according to claim 1, wherein the source of primary radiation provides gamma radiation as the primary radiation.

22. The apparatus according to claim 3, wherein the excitation source is a source of gamma radiation as primary radiation.

* * * * *